(12) United States Patent
Weisshaupt et al.

(10) Patent No.: US 8,986,352 B2
(45) Date of Patent: Mar. 24, 2015

(54) IMPLANT FOR SECURING NEIGHBORING BONE PLATES

(71) Applicant: Aesculap AG, Tuttlingen (DE)

(72) Inventors: Dieter Weisshaupt, Immendingen (DE); Klaus-Dieter Steinhilper, Tuttlingen (DE); Karl-Dieter Lerch, Witten (DE)

(73) Assignee: Aesculap AG, Tuttlingen (DE)

( * ) Notice: Subject to any disclaimer, the term of this patent is extended or adjusted under 35 U.S.C. 154(b) by 139 days.

(21) Appl. No.: 13/775,818

(22) Filed: Feb. 25, 2013

(65) Prior Publication Data

US 2013/0190763 A1     Jul. 25, 2013

Related U.S. Application Data

(63) Continuation of application No. 11/702,258, filed on Feb. 5, 2007, now Pat. No. 8,403,929, which is a continuation of application No. PCT/EP2005/005738, filed on May 27, 2005.

(30) Foreign Application Priority Data

Aug. 4, 2004 (DE) .......................... 10 2004 038 823

(51) Int. Cl.
    *A61B 17/88*     (2006.01)
    *A61B 17/80*     (2006.01)
    (Continued)

(52) U.S. Cl.
    CPC ............. *A61B 17/808* (2013.01); *A61B 17/683* (2013.01); *A61B 17/688* (2013.01); *A61B 17/809* (2013.01); *A61B 17/842* (2013.01);
(Continued)

(58) Field of Classification Search
USPC ............. 606/60, 70–71, 86 A, 103, 144, 148, 606/280–299, 324, 328, 903; 623/17.18–17.19, 23.5
See application file for complete search history.

(56) References Cited

U.S. PATENT DOCUMENTS

| 261,501 A | 7/1882 | Vandermark |
|---|---|---|
| 2,576,649 A | 11/1951 | Slind |

(Continued)

FOREIGN PATENT DOCUMENTS

| DE | 912619 | 5/1954 |
|---|---|---|
| DE | 2125556 | 5/1971 |

(Continued)

OTHER PUBLICATIONS

International Application Serial No. PCT/EP/2005/005738, International Search Report mailed Sep. 19, 2005, 2 pgs.

(Continued)

*Primary Examiner* — Nicholas Woodall
*Assistant Examiner* — Larry E Waggle, Jr.
(74) *Attorney, Agent, or Firm* — RatnerPrestia

(57) ABSTRACT

A method for securing neighboring bone plates by an implant includes the steps of resting an inner contact element of the implant on inner faces of the bone plates, resting an outer contact element of the implant on outer faces of the bone plates, connecting the inner contact element and the outer connecting element by a flexible tensioning element, forming a knot between free strands of the tensioning element, wherein the knot is a slip knot, and pushing the knot in a recess of the outer contact element with the knot being positioned at least partially below an outer surface of the outer contact element.

31 Claims, 4 Drawing Sheets

(51) Int. Cl.
  *A61B 17/68* (2006.01)
  *A61B 17/84* (2006.01)
  *A61B 17/00* (2006.01)
  *A61B 17/04* (2006.01)

(52) U.S. Cl.
  CPC ............... *A61B2017/00004* (2013.01); *A61B 2017/0474* (2013.01)
  USPC ............................................. 606/281; 606/71

(56) References Cited

U.S. PATENT DOCUMENTS

| | | | |
|---|---|---|---|
| 2,856,933 A | 10/1958 | Hildebrand | |
| 3,476,115 A | 11/1969 | Graeff | |
| 3,910,281 A | 10/1975 | Kletschka | |
| 4,177,813 A | 12/1979 | Miller | |
| 4,754,529 A | 7/1988 | Paradis | |
| 4,765,329 A | 8/1988 | Cumming | |
| 4,802,477 A | 2/1989 | Gabbay | |
| 4,966,600 A | 10/1990 | Songer | |
| 5,021,059 A | 6/1991 | Kensey | |
| 5,242,459 A | 9/1993 | Buelna | |
| 5,250,049 A | 10/1993 | Michael | |
| 5,258,011 A | 11/1993 | Drews | |
| 5,350,399 A | 9/1994 | Erlebacher | |
| 5,423,858 A | 6/1995 | Bolanos | |
| 5,433,727 A | 7/1995 | Sideris | |
| 5,454,821 A | 10/1995 | Harm | |
| 5,466,241 A | 11/1995 | Leroy | |
| 5,527,341 A | 6/1996 | Gogolewski | |
| 5,549,620 A | 8/1996 | Bremer | |
| 5,707,373 A | 1/1998 | Sevrain | |
| 5,800,436 A | 9/1998 | Lerch | |
| 5,868,746 A | 2/1999 | Sarver | |
| 5,919,205 A | 7/1999 | Heimberger | |
| 5,921,986 A | 7/1999 | Bonutti | |
| 6,022,351 A | 2/2000 | Bremer | |
| 6,063,106 A | 5/2000 | Gibson | |
| 6,096,058 A | 8/2000 | Boche | |
| 6,258,091 B1 | 7/2001 | Sevrain | |
| 6,270,500 B1 | 8/2001 | Lerch | |
| 6,328,743 B2 | 12/2001 | Lerch | |
| 6,379,363 B1 | 4/2002 | Herrington et al. | |
| 6,514,274 B1 | 2/2003 | Boucher et al. | |
| 6,589,244 B1 | 7/2003 | Sevrain et al. | |
| 6,685,707 B2 | 2/2004 | Roman et al. | |
| 6,755,834 B2 | 6/2004 | Amis | |
| 6,921,401 B2 | 7/2005 | Lerch et al. | |
| 2002/0156475 A1 | 10/2002 | Lerch | |
| 2003/0229349 A1* | 12/2003 | Wellisz et al. | 606/72 |
| 2004/0102779 A1* | 5/2004 | Nesper et al. | 606/72 |
| 2004/0127908 A1 | 7/2004 | Roman | |
| 2004/0210224 A1 | 10/2004 | Ahmad | |
| 2004/0267287 A1 | 12/2004 | Nesper | |
| 2005/0049599 A1 | 3/2005 | Nesper | |
| 2005/0192632 A1* | 9/2005 | Geissler et al. | 606/232 |

FOREIGN PATENT DOCUMENTS

| | | |
|---|---|---|
| DE | 7802791 U1 | 5/1978 |
| DE | 2804070 | 8/1979 |
| DE | 3709067 A1 | 9/1988 |
| DE | 8910462.5 U1 | 2/1990 |
| DE | 4243427 C1 | 3/1994 |
| DE | 69108236 T2 | 8/1995 |
| DE | 29614921 U1 | 11/1996 |
| DE | 69406972 T2 | 7/1998 |
| DE | 29919090 U1 | 1/2000 |
| DE | 19832797 C1 | 2/2000 |
| DE | 19952359 C1 | 3/2001 |
| DE | 10128917 C1 | 10/2002 |
| DE | 10161724 A1 | 7/2003 |
| EP | 0602757 | 6/1994 |
| EP | 0628286 | 12/1994 |
| JP | 05220174 A | 8/1993 |
| WO | WO-0049949 A1 | 8/2000 |

OTHER PUBLICATIONS

U.S. Appl. No. 11/702,258, Notice of Allowance mailed Nov. 27, 2012, 5 pgs.

* cited by examiner

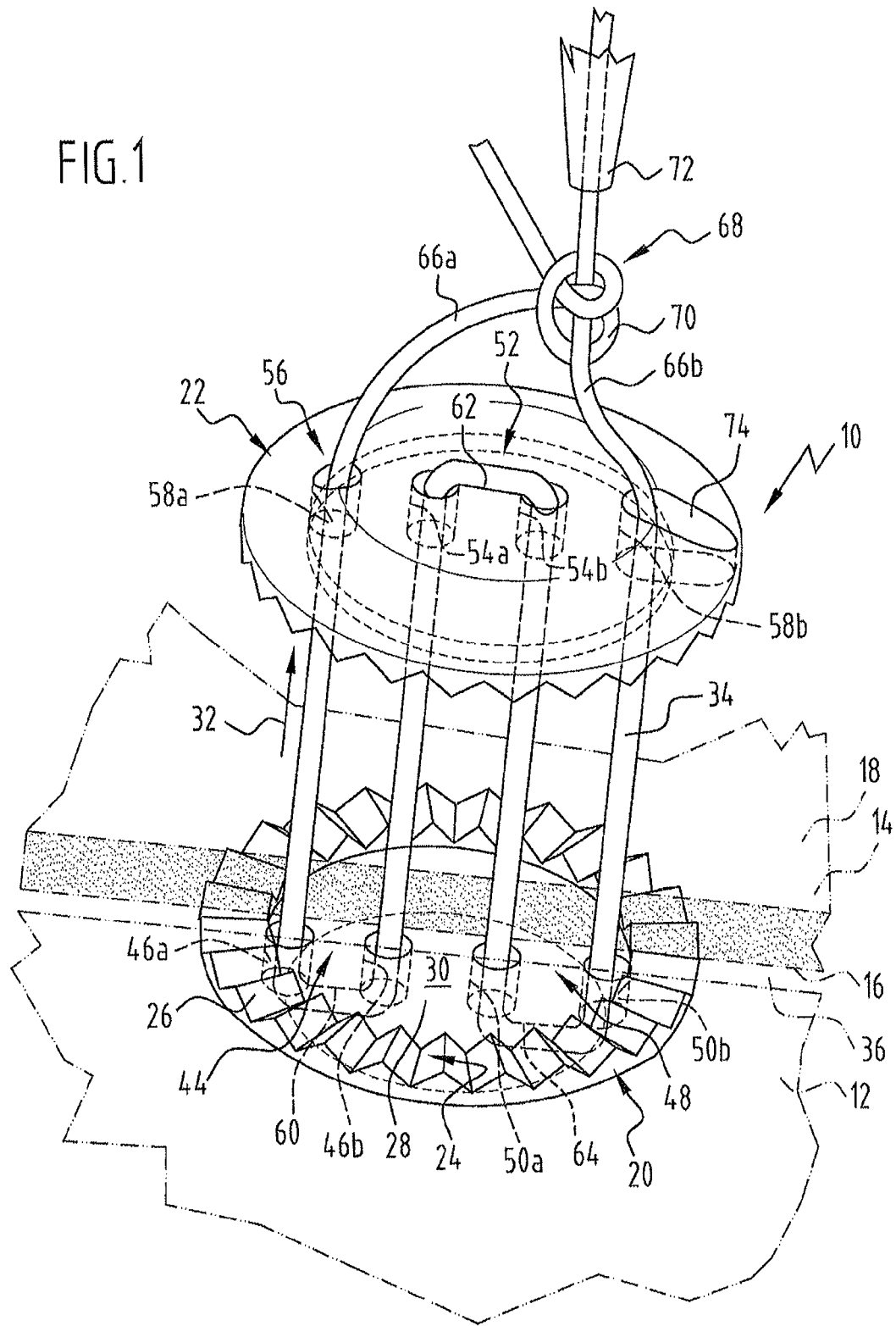

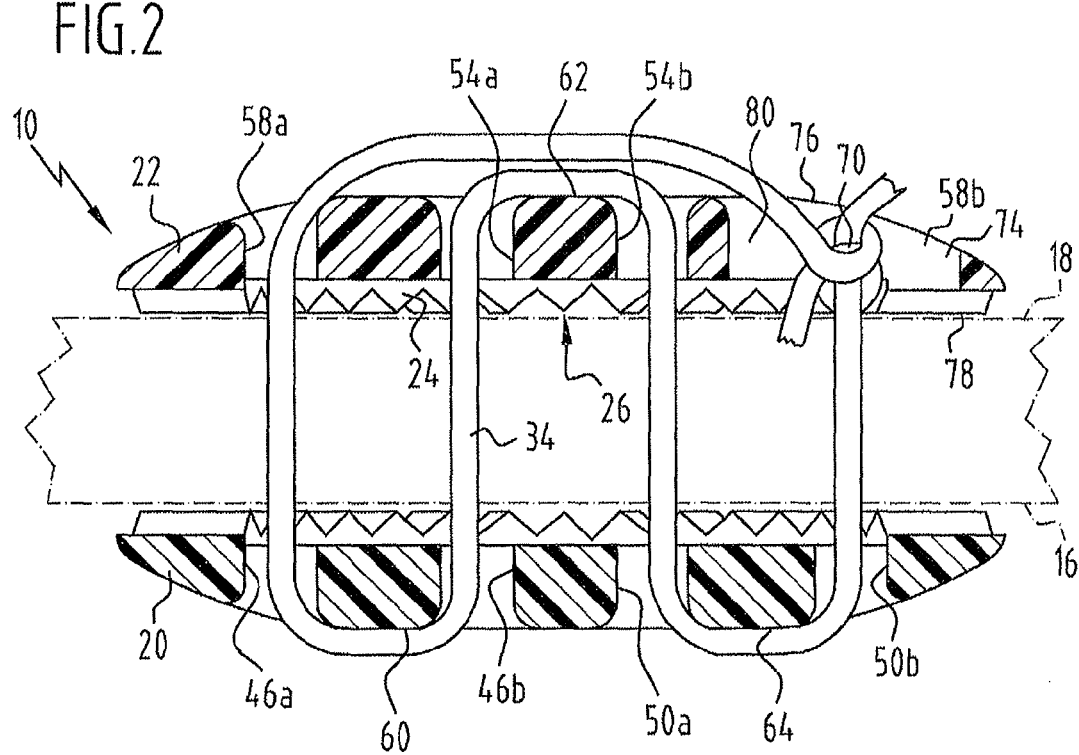
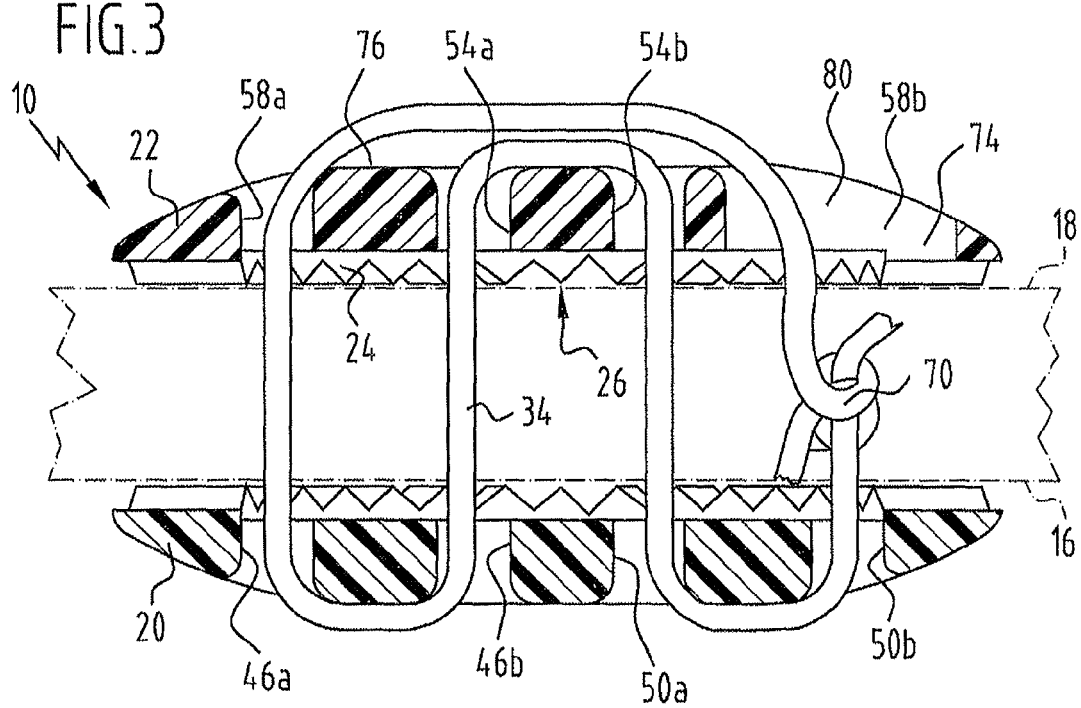

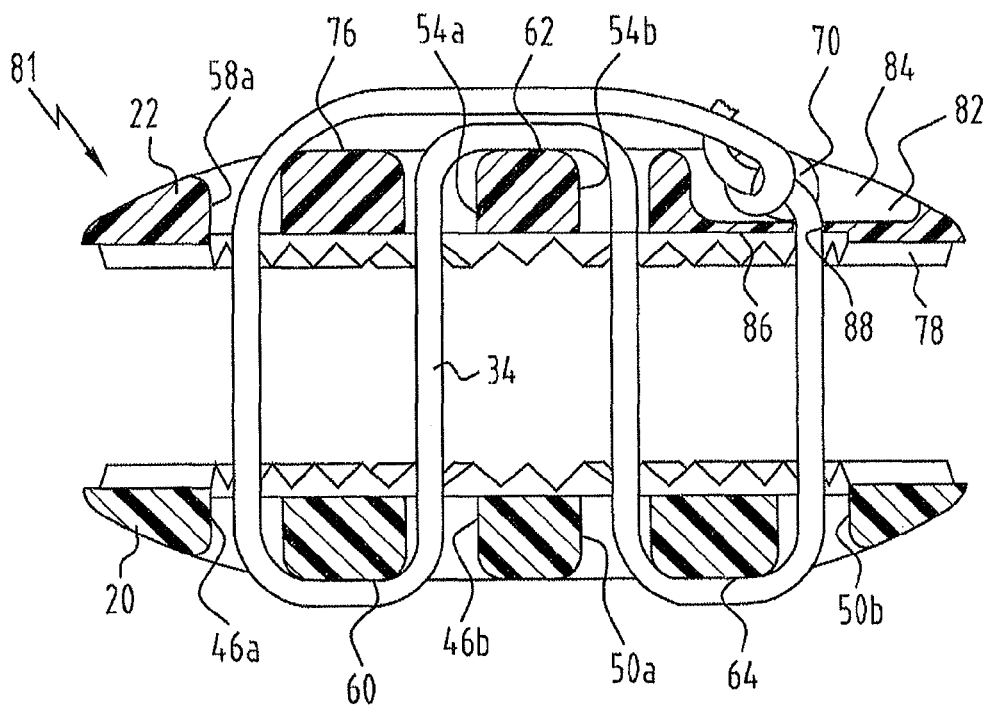
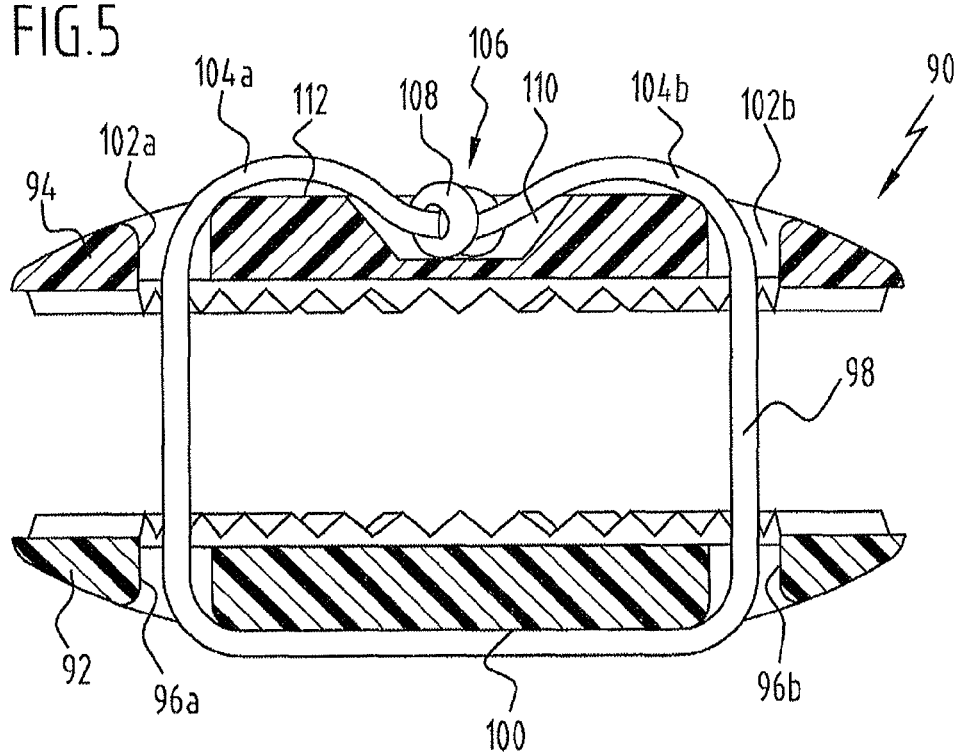

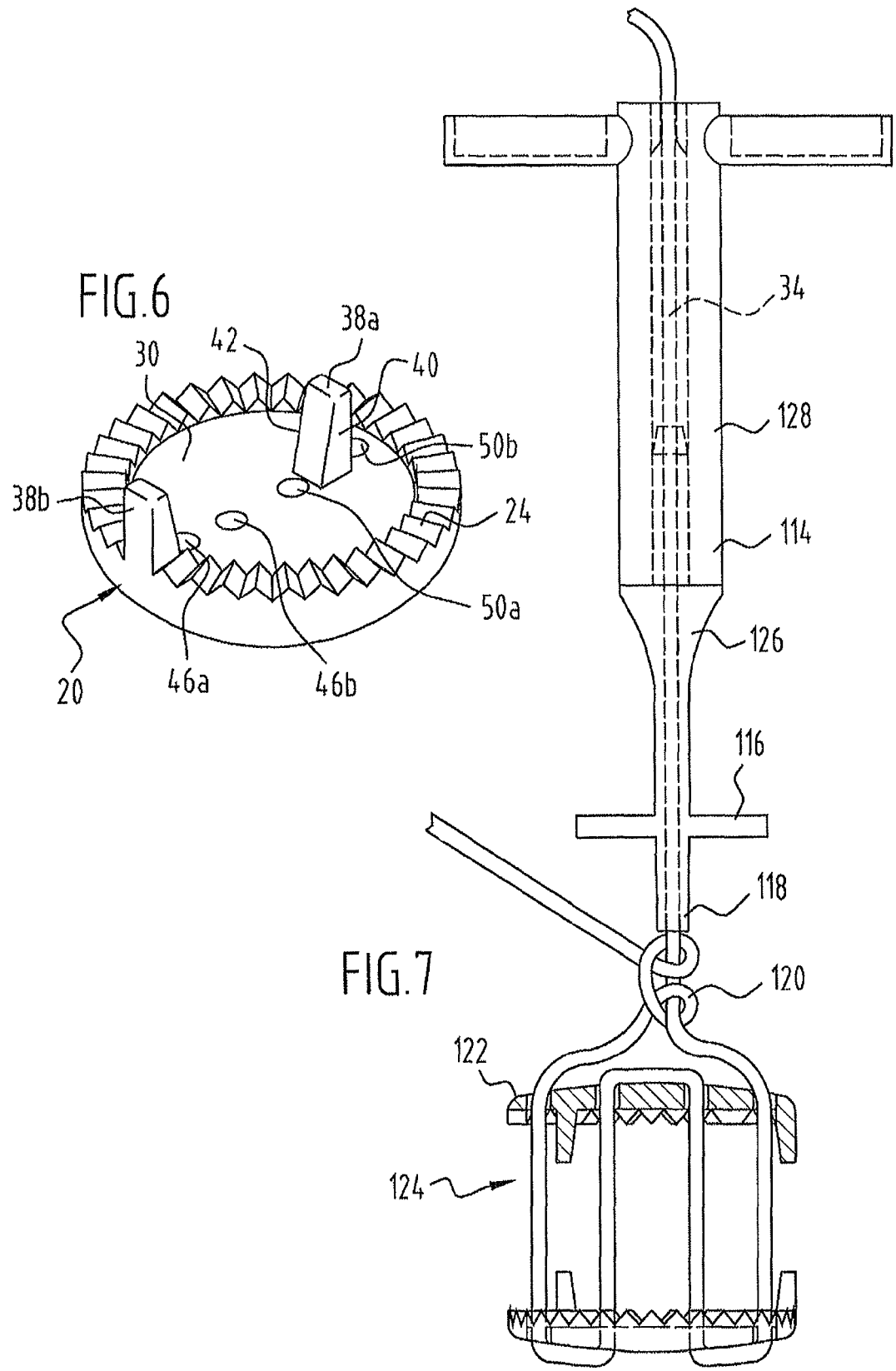

IMPLANT FOR SECURING NEIGHBORING BONE PLATES

RELATED APPLICATIONS

This application is a continuation of U.S. application Ser. No. 11/702,258, filed Feb. 5, 2007, which is a continuation of International Application No. PCT/EP2005/005738, filed May 27, 2005, which claims the benefit of priority of German Application No. 10 2004 038 823.7, filed Aug. 4, 2004. All of the aforementioned applications are incorporated herein by reference in their entirety and for all purposes.

FIELD

The present invention relates to implants and methods for securing neighboring bone plates, and in particular, implants and methods for securing neighboring cranial bone plates.

BACKGROUND

The invention relates to an implant for securing neighboring bone plates, especially neighboring cranial bone plates, wherein each of the bone plates has an inner face and an outer face, comprising an inner contact element that is adapted to rest on the inner face of the neighboring bone plates, an outer contact element that is adapted to rest on the outer faces of the neighboring bone plates and in a linear manner a flexible tensioning element for connecting the inner contact element and the outer contact element in such a manner that they can no longer be separated from one another.

Such an implant is known from DE 199 52 359 C1 (wherein it is referred to as a surgical connecting element).

A further example of such an implant is known from DE 101 28 917 C1.

A procedure for the treatment of a broken bone is known from U.S. Pat. No. 5,921,986, wherein an anchor connected to a thread is fed through the bone on each side of the break, the thread is tensioned in order to transmit a force to a bone on the first side of the break, wherein the thread extends over the break, and wherein a force is transmitted from a second anchor to the bone on a second side of the break.

SUMMARY OF THE INVENTION

In accordance with the invention, an implant with improved properties is provided.

In accordance with an embodiment of the invention, an implant is provided with the outer contact element comprising at least one recess for at least partially accommodating a connection region between the free strands of the tensioning element or for feeding the connection region through into a separation gap between the neighboring bone plates.

The free strands of the flexible linear tensioning element which, in particular, is a thread or a wire are linked by means of the connection region. The resultant formation such as a knot for example, can lead to irritation of the surrounding tissue or there is a danger that this connection region is or will be felt by a patient. In accordance with the invention, there is provided at least one recess with the aid of which the connection region is adapted to be at least partially countersunk relative to the outer surface of the outer contact element. As a consequence thereof, protrusion of the connection region above the outer contact element can be prevented or at least reduced, and thus in turn, tissue irritations can be prevented or at least reduced.

In particular, the at least one recess is formed in such a way that the connection region is positionable at least partially below an outer surface of the outer contact element. In consequence, the connection region (and in particular a knot) can be at least partly sunk with respect to this outer surface.

In particular, the connection region is formed by means of a knot. The free strands can be permanently connected to each other by means of the knot and hence the contact elements are fixed together so that they can no longer be separated from one another.

It is particularly very advantageous if the knot is in the form of a slip knot. It can then be pushed into a desired position and pulled-together with the aid of a slip knot applicator in order to complete the securing process as is described in DE 101 61 724 A1 for example.

It is particularly very advantageous if, whether with or without the recess for the connection region, the connection region is formed by means of a prefabricated slip knot. It can then be supplied to the operating surgeon in the form of a finished manufactured implant which is utilizable in a simple manner. The operating surgeon then only has to position the slip knot at the correct position and tighten a loop. In particular, he does not have to produce a knot himself.

The free strands are preferably those regions of the tensioning element which emanate from the outer contact element. By permanently connecting these free strands, the contact elements can be fixed with respect to one another in such a manner that they cannot be moved apart. As a consequence thereof, the bone plates can then in turn be fixed relative to each other.

Provision may be made for the at least one recess to constitute a through hole. In consequence, a connection region and in particular a knot can be pushed through the recess into the separation gap between the bone plates and accommodated therein so that it will not project above an outer surface of the outer contact element.

Provision may be made for the at least one recess to comprise a seating area for the connection region. This seating area can be trough-shaped for example. By virtue of such a seating area, the connection region can be positioned such that is sunken with respect to an outer surface of the outer contact element.

For example, a base is associated with the at least one recess. The connection region can be prevented from being pushed into the separation gap by means of this base.

It is expedient for the inner contact element to comprise at least two spaced feed-through recesses for the tensioning element. By virtue of the feed-through recesses, the tensioning element can be held on the inner contact element and a means for altering the direction of the tensioning element can be provided.

In particular, the tensioning element is placed on a surface of the inner contact element between the feed-through recesses. By virtue of the corresponding placement region, the inner contact element can be displaced relative to the outer contact element by means of the tensioning element and the two contact elements can be tensioned towards one another.

Provision is made, in particular, for the outer contact element to comprise at least two spaced feed-through recesses for the tensioning element. Thus, for example, the free strands of the tensioning element can thereby be fed through the outer contact element.

It is expedient for the at least one recess for the connection region to be formed at a feed-through recess or to form a feed-through recess. As a consequence thereof, only a minimized number of openings through the outer contact element need be provided, this thereby increasing the mechanical stability. Furthermore, the production process is simplified.

It is particularly very advantageous, if the tensioning element is guided on the inner contact element and the outer contact element in such a way that a pulley-block system is formed. On the one hand thereby, a secure tensioning arrangement between the contact elements can be achieved by means of the tensioning element and thus secure fixing of the neighboring bone plates is obtained. On the other hand, purposeful guidance of the outer contact element and the inner contact element relative to one another during a tensioning process can be achieved, this thereby facilitating the work for an operating surgeon. Furthermore, relatively large tensional forces can be applied, this thereby resulting in the contact elements exerting large clamping forces on the bone plates held therebetween. In consequence, the bone plates are held securely between the contact elements and hence secure fixing of the bone plates relative to one another is obtained.

It is expedient, if, in combination with the at least one recess for the connection region or even without such a recess, the inner contact element comprises a first pair of spaced feed-through recesses for the tensioning element between which the tensioning element rests on the inner contact element in a first placement region, if the inner contact element comprises a second pair of neighboring feed-through recesses for the tensioning element between which the tensioning element rests on the inner contact element in a second placement region, if the outer contact element comprises a first pair of neighboring feed-through recesses for the tensioning element between which the tensioning element rests on the outer contact element in a third placement region, and if the outer contact element comprises a second pair of spaced feed-through recesses through which the free strands of the tensioning element are fed. By virtue of such an arrangement of feed-through recesses, the tensioning element can be guided through a first turn on the inner contact element, then diverted towards the outer contact element, rest on the outer contact element in the course of a further turn and then be diverted back to the inner contact element and from there, after a further turn, be diverted yet again towards the outer contact element. A pulley-block-like system can thereby be formed, and this can be employed in an advantageous manner. For example, large clamping forces can be exerted and correct guidance of the outer contact element by means of the tensioning element is assured thereby simplifying the employment of the arrangement for an operating surgeon.

In particular, the first pair of feed-through recesses in the outer contact element is arranged between the feed-through recesses of the second pair. Thus, a turn of the tensioning element between the feed-through recesses of the first pair can be formed so as to enable a pulley-block system to be formed once again.

It is advantageous for the feed-through recesses of the inner contact element to be arranged in a line. They are then aligned. In consequence, the regions of the tensioning element which pass through the separation gap are parallel and aligned. The employment thereof is thereby simplified. For example, one or more contact elements (which are arranged on the inner contact element and/or on the outer contact element) can then be used in a simple manner in order to hold the oppositely located bone plates apart in the region of the separation gap between the contact elements so that the tensioning element cannot get trapped between the bone plates. Thus, for example, it is thereby ensured once again that, in the course of exerting a pulling force on the tensioning element, the contact elements will move relative to one another in order to hold the neighboring bone plates therebetween in a clamping manner.

For the same reason, it is expedient for the feed-through recesses in the outer contact element to be arranged in a line.

It is expedient if the feed-through recesses of the first pair in the outer contact element and the neighboring feed-through recesses of the first pair and the second pair in the inner contact element are mutually matched. In consequence, the tensioning element can be guided in such a way that a pulley-block system can be realized.

For the same reason, it is expedient if the feed-through recesses of the second pair in the outer contact element and non-neighboring feed-through recesses of the first pair and the second pair in the inner contact element are mutually matched.

It is expedient if the at least one recess for the connection region is arranged in a feed-through recess of the second pair of the outer contact element or forms such a feed-through recess. As a consequence thereof, the formation of the pulley-block system is not affected by the recess. Furthermore, through holes in the outer contact element, which could in principle affect the mechanical stability thereof, can be minimized.

Provision may be made for the at least one recess for the connection element to be arranged such that it is displaced relative to the first pair of feed-through recesses. In consequence, the position of a tensioning element region near a turn or a loop of the tensioning element, which rests on the surface of the outer contact element, can be displaced.

Provision is made for the first placement region and the second placement region to lie on a surface of the inner contact element that is remote from the outer contact element. The inner contact element can thereby be pulled against the outer contact element with the aid of the tensioning element.

Provision may also be made for the third placement region to lie on a surface of the outer contact element that is remote from the inner contact element. In consequence, a pulley-block system can then be formed.

In particular, the tensioning element is guided through the outer contact element in displaceable manner. A pulling force can then be exerted by means of which the spacing between the inner contact element and the outer contact element is reducible and a clamping force is adapted to be exerted on the bone plates located therebetween. The tensioning element tracks said decrease of the spacing so as to thereby enable a clamping force to be applied.

In particular, the inner contact element is displaceable with respect to the outer contact element when the tensioning element is tensioned.

It is expedient for the tensioning element to be provided for passing through the separation gap between the bone plates. This gap makes the appropriate space available for enabling the tensioning element to be accommodated in the region between the contact elements.

It is particularly very advantageous, if the inner contact element and/or the outer contact element comprises at least one spacer for the bone plates which is adapted to project into the separation gap. In consequence, the bone plates can be kept apart at the separation gap between the contact elements, namely, in such a manner that the tensioning element can penetrate freely through the separation gap. This in turn thereby prevents the tensioning element from getting jammed between the bone plates. By exerting a pulling force for example, the contact elements can then be moved relative to one another so as in turn to thereby enable bone plates to be clamped therebetween. Preferably, the at least one spacer is in line with the feed-through recesses for the tensioning element in order to ensure free guidance of the tensioning element in the separation gap.

Provision may be made for the inner contact element and/or the outer contact element to be curved in such a manner that an intermediary space is formed between a region of contact with a bone plate and the region holding the contact region. It is thereby possible for example, to change to a certain extent the height of the contact element itself by the application of force. For example, the height is reduced during the fixing process. When the force abates, then the height increases. This can provide for an additional tensioning effect which improves the securement of the bone plates between the contact elements.

It is then expedient if the inner contact element and/or the outer contact element is resilient taken with reference to a connection region. It is thereby possible for the clamping effect to be improved.

It is expedient for the inner contact element and/or the outer contact element to have a gripping area at a region of contact with a bone plate. This gripping area provides for an improved gripping effect on the bone plate. The gripping area can be formed by means of ribbing, a roughened area or a set of teeth for example.

In particular the gripping area is arranged in peripheral manner, i.e. it is arranged around the periphery of the corresponding contact element. This thus results in a symmetrical arrangement of the contact element which simplifies its employment.

It is expedient if the tensioning element is made of a resorbable material.

The following description of preferred embodiments serves for a more detailed explanation of the invention when taken in conjunction with the drawings.

BRIEF DESCRIPTION OF THE DRAWINGS

FIG. 1 shows a schematic perspective illustration of a first exemplary embodiment of an implant in accordance with the invention;

FIG. 2 is a sectional view of the implant in accordance with FIG. wherein the bone plates are secured and a knot is sunk in a recess;

FIG. 3 is the same view as FIG. 2, but wherein the knot is located in a separation gap between fixed bone plates;

FIG. 4 is a sectional view of a second exemplary embodiment;

FIG. 5 is a sectional view of a third exemplary embodiment;

FIG. 6 is a perspective illustration of a variant of a contact element and the implant in accordance with FIG. 1; and FIG. 7 is a schematic illustration of an exemplary embodiment of an implant and a slip knot applicator.

DETAILED DESCRIPTION

A first exemplary embodiment of an implant in accordance with the invention is shown in FIGS. 1 to 3 and bears the general reference 10 therein. The implant serves for securing neighboring bone plates 12, 14. The bone plates 12, 14 are, in particular, cranial bone plates; for brain operations, a cranial bone plate is sawn out in order to gain access to the brain. After completion of the brain operation, the cranial bone plate that had been removed (for example the bone plate 12) must be fixed back to the bone plates surrounding it (for example the bone plate 14 and further bone plates). This is effected with the aid of a plurality of implants 10.

The bone plates 12, 14 each have an inner surface 16 and an opposite outer surface 18. The inner surface 16 faces towards the interior of the body; in the case of a cranial bone plate, the inner surface 16 faces towards the brain.

The implant 10 comprises an inner contact element 20 that is adapted to rest on the inner surface 16 of the bone plates 12 and 14. Furthermore, the implant 10 comprises an outer contact element 22 that is adapted to rest on the outer surfaces 18 of the bone plates 12 and 14.

In the exemplary embodiment shown, the inner contact element 20 and the outer contact element 22 have a circular cross section. They are formed in a substantially identical manner insofar as their general shape is concerned.

The inner contact element 20, similar to the outer contact element 22, has an annular contact region by means of which it rests against the inner surface 16 of the bone plates 12, 14. This contact region 24 comprises a gripping area 26 which is formed "non-smoothly". This gripping area 26 serves the purpose of improving the bite of the inner contact element 20 on the inner surface 16 of the bone plates 12, 14 or of the outer contact element 22 on the outer surfaces 18 of the bone plates 12, 14 and in particular it serves to prevent slipping. For example, the gripping area 26 is formed by means of a set of peripherally extending teeth, ribbing or a roughened surface.

The inner contact element 20 (and, in the exemplary embodiment shown, the outer contact element 22 too) are curved, namely, in such a manner that an intermediary space 30 is formed between the contact region 24 and a region 28 holding it, in particular, in one-piece manner.

Provision may be made for the inner contact element 20 and/or the outer contact element 22 to be resilient taken with reference to a connecting direction 32 between the two contact elements 20 and 22. This can improve the securement of the contact elements 20 and 22 together and thus the securement of the bone plates 12 and 14 located between the contact elements 20 and 22.

For the purposes of connecting the inner contact element 20 and the outer contact element 22, there is provided (at least) one linearly flexible tensioning element 34. The tensioning element is, in particular, a surgical thread or a wire. The tensioning element serves for the purpose of connecting the two contact elements 20 and 22 together in such a manner that they can no longer be separated from one another (and thus to fix the bone plates 12 and 14 relative to one another), whereby the inner contact element 20 is displaceable with respect to the outer contact element 22 by pulling the tensioning element 34.

The tensioning element 34 is made, in particular, of a material that is resorbable in the body.

The tensioning element 34 passes through a separation gap 36 between the neighboring bone plates for the purpose of securing the bone plates 12, 14.

Hereby, provision may be made for the inner contact element 20 and/or the outer contact element 22 to comprise at least one spacer 38a, 38b (FIG. 6) which serves to project into the separation gap 36. The end face of the bone plate 12 then rests against a first contact face 40 of the spacer or spacers 38a, 38b and the end face of the neighboring bone plate 14 rests against an opposing second contact face 42 of the spacer or spacers 38a, 38b. The spacer or the spacers 38a, 38b hold the bone plates 12, 14 apart so that the tensioning element 34 can pass freely through the separation gap 36 in such a manner that tension can be exerted and in order to prevent the tensioning element 34 from jamming against the bone plates 12, 14 in the separation gap 36.

The spacer or the spacers 38a, 38b are located, in particular, in line with feed-through recesses for the tensioning element 34 as will be described in more detail hereinbelow.

The spacer or the spacers 38a, 38b is or are formed, in particular, in one-piece manner with the associated contact element 20, 22.

The inner contact element 20 of the implant 10 comprises a first pair 44 of spaced neighboring feed-through recesses 46a, 46b and comprises a second pair 48 of spaced neighboring feed-through recesses 50a, 50b. The feed-through recesses 46b and 50a are inwardly located feed-through recesses and the feed-through recesses 46a, 50b are outwardly located feed-through recesses. The feed-through recess 46b neighbors the feed-through recess 50a. The distance between the feed-through recesses 46a and 50b corresponds to the largest distance between feed-through recesses. The feed-through recesses 46b and 50a are located between the feed-through recesses 46a and 50b.

The feed-through recesses 46a, 46b, 50a and 50b are arranged, in particular, along a line (in common with the spacer or the spacers 38a, 38b) so that those tensioning element regions of the tensioning element 34 that are located in the separation gap 36 between the inner contact element 20 and the outer contact element 22 can be positioned so as to be orientated in parallel with one another and aligned with one another.

The outer contact element 22 comprises a first pair 52 of spaced neighboring feed-through recesses 54a, 54b. Furthermore, the outer contact element 22 comprises a second pair 56 of spaced feed-through recesses 58a, 58b. Hereby, the first pair 52 of the feed-through recesses 54a and 54b are located between the feed-through recesses 58a and 58b. The feed-through recesses 58a, 58b of the second pair 56 are outwardly located feed-through recesses; the feed-through recesses 54a, 54b of the first pair 52 are inwardly located feed-through recesses. The feed-through recesses 54a and 58a are neighbors and the feed-through recesses 54b and 58b are neighbors. The distance between the feed-through recesses 58a and 58b of the second pair 56 corresponds to the maximum distance between feed-through recesses in the outer contact element 22.

The feed-through recesses 54a, 54b, 58a and 58b of the outer contact element 22 are matched to the arrangement of the feed-through recesses 46a, 46b, 50a, 50b of the inner contact element 20. In particular, neighboring feed-through recesses (58a and 54a; 54a and 54b; 54b and 58b) in the outer contact element 22 have the same spacing as the corresponding feed-through recesses (46a and 46b; 46b and 50a; 50a and 50b) in the inner contact element 20. Furthermore, the feed-through recesses 54a, 54b, 58a, 58b in the outer contact element 22 are preferably located in a line.

Due to the matched formation of the feed-through recesses of the inner contact element 20 and those of the outer contact element 22, a parallel and aligned guidance of the tensioning element 34 between the contact elements 20 and 22 can be achieved.

The tensioning element 34 is formed in one-piece manner in the exemplary embodiment shown in FIGS. 1 to 3. (It is also fundamentally possible for separate tensioning elements to be provided.) The tensioning element 34 is fed through the feed-through recess 54a in the outer contact element 22 and through the feed-through recess 46a in the inner contact element 22. From the feed-through recess 46a, it is then fed to the feed-through recess 46b and passed through the latter. Between the feed-through recesses 46a and 46b, the tensioning element 34 is located in a first placement region 60 and rests on an outer surface of the inner contact element 20 that is remote from the outer contact element 22. From the feed-through recess 46b, the tensioning element 34 is fed to the feed-through recess 54a of the outer contact element 22 and passed therethrough.

From the feed-through recess 54a, the tensioning element 34 is fed to the neighboring feed-through recess 54b and passed therethrough. Between the feed-through recesses 54a, 54b, the tensioning element 34 is located in a third placement region 62 and rests on an outer surface of the outer contact element 22 which is remote from the inner contact element 20.

The tensioning element 34 is fed through the feed-through recess 54b up to the feed-through recess 50a and is passed therethrough. From the feed-through recess 50a, the tensioning element 34 is fed to the feed-through recess 50b and passed therethrough. Between the feed-through recess 50a and 50b, the tensioning element is located in a second placement region 64 on the outer surface of the inner contact element 20.

From the feed-through recess 50b, the tensioning element 34 is fed to the feed-through recess 58b and passed therethrough.

Starting from the feed-through recesses 58a and 58b, the tensioning element 34 has free strands, namely, a first free strand 66a (outgoing from the feed-through recess 58a) and a free strand 66b (outgoing from the feed-through recess 58b).

When the neighboring bone plates 12 and 14 are secured to one another by means of the implant 10, those regions of the tensioning element 34 that are fed between the feed-through recesses 58a and 46a, 46b and 54a, 54b and 50a and also 50b and 58b are then, for the greater part, located in the separation gap 36. The tensioning element 34 is guided by the first pair 44 of feed-through recesses 46a, 46b in the inner contact element 20 into the form of a first loop or turn and, outgoing from the inner contact element 20, the direction of the tensioning element 34 is diverted towards the outer contact element 22.

The tensioning element 34 is guided by the first pair 52 of feed-through recesses 54a, 54b into the form of a second loop or turn in order to divert the tensioning element 34 from the outer contact element 22 towards the inner contact element 20.

The tensioning element 34 is guided by the second pair 48 of feed-through recesses 50a, 50b in the inner contact element 20 into the form of a third loop or turn in order to divert the tensioning element 34 yet again from the inner contact element 20 towards the outer contact element 22.

The free strands 66a, 66b are then fed out from the outer contact element 22 via the second pair 56 of feed-through recesses 58a, 58b therein.

A pulley-block system is formed by virtue of this form of guidance of the tensioning element 34 on the contact elements 20 and 22 and between the contact elements 20 and 22; when, for example, the free strands 66a, 66b are pulled (in the direction 32 for example), then the inner contact element 20 is thereby displaced in the direction of the outer contact element 22. In consequence, a clamping force can be exerted on bone plates 12, 14 lying between the contact elements 20, 22 in order to secure them together.

For the purposes of establishing this clamping effect in such a manner that the bone plates 12, 14 can no longer be separated from one another, i.e. the inner contact element 20 and the outer contact element 22 can no longer be separated from one another, provision is made for the free strands 66a, 66b of the tensioning element 34 to be connected. This connection, which, in particular, is formed by means of a knot 70, is effected in a connection region 68.

The knot 70 is preferably in the form of a slip knot which, for example, is adapted to be pushed onto the outer contact element 22 by means of a slip knot applicator (FIG. 7; an operative tip 72 of such a slip knot applicator is indicated in FIG. 1).

An example of a usable slip knot is a Roeder knot.

In the case of the implant 10, provision is preferably made for the knot 70 and in particular a slip knot to be prefabricated, i.e. the implant 10 is implemented with the inner contact element 20, the outer contact element 22 and the tensioning element 34 guided in the manner described above. Furthermore, the free strands 66a, 66b are already connected together by means of a slip knot.

The (slip-) knot 70 can be displaced on the outer contact element 22 by means of the slip knot applicator and the two contact elements 20 and 22 can be fixed relative to one another by, for example, tightening the knot via a free end of the tensioning element 34.

If the inner contact element 20 and/or the outer contact element 22 is resilient, then a force can be exerted during the fixing process which reduces the distance between the outer surfaces of the inner contact element 20 and the outer contact element 22 due to the resilient deformation thereof. When this force is removed, then this distance readily increases. A kind of pre-tensioning process can thereby be effected.

The outer contact element 22 comprises a recess 74 which serves for accommodating or pushing through the connection region 68 of the tensioning element 34, i.e. for the accommodation or the through passage of the knot 70. The recess 74 is formed in such a way that the connection region 68 is positionable at least partly below an outer surface of the outer contact element 22. As a consequence thereof, the connection region 68 (and in particular, the knot 70) does not project above this surface or does so to only a small extent. Irritation of the surrounding tissue due to a knot 70 lying on the implant 10 can then be prevented since the knot 70 is adapted to be "countersunk" due to the recess 74. Furthermore, the danger that a patient will become aware of the knot 70 (in the form of the connection region 68) after a certain period of time is overcome.

The recess 74 is preferably arranged at an outer region of the outer contact element 22 whereat the outer contact element 22 is strengthened. This thereby ensures that the recess 74 will not impair the mechanical stability of the outer contact element 22.

Preferably, the recess 74 is located at or forms the feed-through recess 58b. The recess 74 can be then used directly as a feed-through recess. The complexity of the manufacturing process is thereby reduced. Furthermore, mechanical stability is ensured.

It is also possible for the outer contact element 22 to comprise a plurality of such recesses 74. This may be necessary for example, when two separate tensioning elements are provided for connecting the two contact elements.

In principle, it is also possible for the inner contact element 20 to be provided with such a recess 74 or several recesses. Provision may be made for the inner contact element 20 and the outer contact element 22 to be of identical construction. A recess 74 in the inner contact element 20 has no functional purpose, but nevertheless it is not harmful to the securement of the neighboring bone plates 12 and 14. If only one type of contact element has to be manufactured, then the manufacturing costs can be reduced and the production process is simplified.

In the exemplary embodiment shown in FIGS. 1 to 3, the recess 74 constitutes a through hole, i.e. it goes from an upper surface 76 of the outer contact element 22 to a lower surface 78 of the outer contact element 22. A passage 80 extending through the outer contact element 22 is then formed through which the knot 70 can be pushed.

An intermediate position is shown in FIG. 2 whereat the knot 70 is located in the passage 80. The knot 70 can be moved from there into the separation gap 36 (FIG. 3). The knot 70 does not thereby project above the upper surface 76 of the implant 10.

The implant 10 functions as follows:

The contact elements 20 and 22 are connected "loosely" together by the tensioning element 34, a slip knot 70 having preferably been prefabricated in the free strands 66a, 66b. When the neighboring bone plates 12, 14 are to be secured together, the inner contact element 20 is then placed under the bone plates 12, 14 or a free bone plate is placed on the positioned inner contact element 20.

The tensioning element 34 then runs in the separation gap 36.

The free strands 66a, 66b are pulled in order to reduce the distance between the outer contact element 22 and the inner contact element 20. The inner contact element 20 can thereby be pressed against the inner surfaces 16 of the bone plates 12, 14 and the outer contact element 22 against the outer surfaces 18 of the bone plates 12 and 14.

For the purposes of securing this position, the slip knot 70 is pushed onto the outer contact element 22 by means of a slip knot applicator for example, and it is thereby pushed into the recess 74. From there, the knot 70 can be pushed into the separation gap 36 so that it does not project above the outer contact element 22.

The knot 70 is tightened by pulling on a free end of the tensioning element 34.

Protruding portions of the tensioning element 34 can then be cut off.

In a second exemplary embodiment 81 which is shown in the form of a schematic sectional view in FIG. 4, a recess 82 which is not a through hole is provided in the outer contact element 22. (The same reference symbols as were used for similar elements in the exemplary embodiment in accordance with FIGS. 1 to 3 are used here.) The recess 82 comprises a seating area 84 for the knot 70. The knot 70 is adapted to be inserted into this, for example, trough-shaped seating area 84 so that it does not project above the upper surface 76 of the outer contact element 22 or at most, only partly projects thereabove.

Associated with the recess 82 and thus the seating area 84, there is a base 86 which closes the seating area 84 at the lower surface 78 of the outer contact element 22.

In the base 86, there is formed a feed-through recess 88 through which the tensioning element 34 is fed although the knot 70 cannot enter it. (The feed-through recess 88 corresponds to the feed-through recess 58b in the exemplary embodiment of FIGS. 1 to 3.) Starting from the second placement region 64, the tensioning element 34 is fed through the feed-through recess 88 and thus through the outer contact element 22 towards the inner contact element 20.

In other respects, the implant 81 in accordance with this exemplary embodiment functions as described above.

In a third exemplary embodiment of an implant which is shown in the form of a schematic sectional view in FIG. 5 and bears the general reference 90 therein, there is provided an inner contact element 92 and an outer contact element 94. The inner contact element comprises a first feed-through recess 96a and a second spaced neighboring feed-through recess 96b. A flexible linear tensioning element 98 such as a thread or a wire for example is again provided as the connecting element. This tensioning element 98 is located between the feed-through recesses 96a and 96b on an outer surface of the inner contact element in a placement region 100 when the contact elements 92 and 94 are tensioned towards one another.

The outer contact element 94 comprises a first feed-through recess 102a and a second spaced neighboring feed-through recess 102b which are matched to the arrangement of the feed-through recesses 96a, 96b in the inner contact element 92.

The tensioning element 98 is fed from the feed-through recess 102a of the outer contact element 94 to the feed-through recess 96a of the inner contact element 92 and then guided through this feed-through recess 96a. It is fed on further between the feed-through recesses 96a and 96b in the form of a loop or a turn and rests against the inner contact element 92 in the placement region 100. It is diverted towards the outer contact element 94 at the feed-through recess 96b through which it is fed. It is fed through the feed-through recess 102b in said outer contact element.

Free strands 104a, 104b of the tensioning element 98 are led out from the respective feed-through recesses 102a and 102b. They are connected together by a connection region 106 and in particular, a knot 108, in order to connect the free strands 104a, 104b together and thus secure the mutually fixed position of the two contact elements 92 and 94.

An, in particular, trough-shaped recess 110 is formed in the outer contact element 94 between the feed-through recesses 102a and 102b. The knot 108 can be inserted into this recess 110 so that it does not project above an upper surface 112 of the outer contact element 94 or at most, projects only partially thereabove.

In other respects, the implant 90 functions in the same manner as in the exemplary embodiments described above.

The use of a slip knot applicator 114 is indicated schematically in FIG. 7. This comprises a flange 116. Furthermore, it comprises an applicator tip 118 with the aid of which a force can be exerted on a slip knot 120 in order to shift the latter towards an outer contact element 122 of an implant 124.

Basically, the implant 124 is constructed in the manner described above.

For example, the applicator tip 118 is seated on a sliding member 126 of the slip knot applicator 114. A handle element 128 is connected to the sliding member 126. In one exemplary embodiment, the connection is such that the connection between the handle element 128 and the sliding member 126 will release when a certain displacement force is exceeded. Such a slip knot applicator (a device for pushing together a loop of a thread which is in the form of a slip knot that is formed by the distal free end of the thread and is displaceable along the thread) is described in DE 101 61 724 A1 to which reference is expressly made.

With the aid of the slip knot applicator, it is possible to hold the tensioning element 34, which is threaded through the handle element 128 below the sliding member 126, at a proximal end thereof and to pull a slip knot 120 together by means of the applicator tip 118 (i.e. to form a firm knot by pulling a loop together).

What is claimed:

1. A method for securing neighboring bone plates, wherein the bone plates each have an inner face and an outer face, by an implant, comprising:
    resting an inner contact element of the implant on the inner faces of the bone plates;
    resting an outer contact element of the implant on the outer faces of the bone plates;
    connecting the inner contact element and the outer connecting element by a flexible tensioning element;
    forming a knot between free strands of the tensioning element, wherein the knot is a slip knot; and
    pushing the knot in a recess of the outer contact element with the knot being positioned at least partially below an outer surface of the outer contact element, wherein the knot is pushed through the recess into a separation gap between the neighboring bone plates.

2. The method in accordance with claim 1, wherein the knot is prefabricated.

3. The method in accordance with claim 1, wherein the free strands are those regions of the tensioning element which emanate from the outer contact element.

4. The method in accordance with claim 1, wherein the recess for the knot constitutes a through hole.

5. The method in accordance with claim 1, wherein the recess comprises a seating area for the knot.

6. The method in accordance with claim 5, wherein a base is associated with the recess.

7. The method in accordance with claim 1, wherein the inner contact element comprises at least two spaced feed-through recesses for the tensioning element.

8. The method in accordance with claim 7, wherein the tensioning element rests on a surface of the inner contact element between the feed-through recesses.

9. The method in accordance with claim 1, wherein the outer contact element comprises at least two spaced feed-through recesses for the tensioning element.

10. The method in accordance with claim 9, wherein the recess for the knot is formed at a feed-through recess or forms a feed-through recess.

11. The method in accordance with claim 1, wherein the tensioning element is guided on the inner contact element and the outer contact element in such a way that a pulley block system is formed.

12. The method in accordance with claim 1, wherein the inner contact element comprises a first pair of spaced feed-through recesses between which the tensioning element rests on the inner contact element in a first placement region, the inner contact element comprises a second pair of neighboring feed-through recesses for the tensioning element between which the tensioning element rests on the inner contact element in a second placement region, the outer contact element comprises a first pair of neighboring feed-through recesses for the tensioning element between which the tensioning element rests on the outer contact element in a third placement region, and the outer contact element comprises a second pair of spaced feed-through recesses through which the free strands of the tensioning element are fed.

13. The method in accordance with claim 12, wherein the first pair of feed-through recesses in the outer contact element is arranged between the feed-through recesses of the second pair.

14. The method in accordance with claim 12, wherein the feed-through recesses of the inner contact element are arranged in a line.

15. The method in accordance with claim 12, wherein the feed-through recesses of the outer contact element are arranged in a line.

16. The method in accordance with claim 12, wherein the feed-through recesses of the first pair in the outer contact element and the neighboring feed-through recesses of the first pair and the second pair in the inner contact element are mutually matched.

17. The method in accordance with claim 12, wherein the feed-through recesses of the second pair in the outer contact element and the non-neighboring feed-through recesses of the first pair and the second pair in the inner contact element are mutually matched.

18. The method in accordance with claim 12, wherein the recess for the knot is arranged at a feed-through recess of the second pair in the outer contact element or forms such a feed-through recess.

19. The method in accordance with claim 12, wherein the recess for the knot is arranged such that it is displaced relative to the first pair of feed-through recesses.

20. The method in accordance with claim 12, wherein the first placement region and the second placement region are located on a surface of the inner contact element that is remote from the outer contact element.

21. The method in accordance with claim 12, wherein the third placement region is located on a surface of the outer contact element that is remote from the inner contact element.

22. The method in accordance with claim 1, wherein the tensioning element is guided through the outer contact element in a displaceable manner.

23. The method in accordance with claim 1, wherein the inner contact element is displaced towards the outer contact element when the tensioning element is tensioned.

24. The method in accordance with claim 1, wherein the tensioning element passes through the separation gap between the bone plates.

25. The method in accordance with claim 1, wherein at least one of the inner contact element and the outer contact element comprises at least one spacer for the bone plates which projects into the separation gap between the bone plates.

26. The method in accordance with claim 25, wherein the at least one spacer lies along a line with feed-through recesses.

27. The method in accordance with claim 1, wherein at least one of the inner contact element and the outer contact element is curved in such a manner that an intermediary space is formed between a region of contact with a bone plate and the region incorporating the contact region.

28. The method in accordance with claim 1, wherein at least one of the inner contact element and the outer contact element is resilient taken with reference to a connecting direction.

29. The method in accordance with claim 1, wherein at least one of the inner contact element and the outer contact element comprises a gripping area at the region of contact with a bone plate.

30. The method in accordance with claim 29, wherein the gripping area is formed in a peripheral manner.

31. The method in accordance with claim 1, wherein the tensioning element is made of a resorbable material.

* * * * *